US005480797A

United States Patent [19]

Francavilla et al.

[11] Patent Number: 5,480,797

[45] Date of Patent: Jan. 2, 1996

[54] AUGMENTER OF LIVER REGENERATION (ALR)

[75] Inventors: Antonio T. Francavilla, Pittsburgh, Pa.; Michio Hagiya, Shiga, Japan; Thomas E. Starzl, Pittsburgh, Pa.

[73] Assignees: Toyobo Co., Ltd., Osaka, Japan; University of Pittsburgh, Pittsburgh, Pa.

[21] Appl. No.: 197,496

[22] Filed: Feb. 16, 1994

[51] Int. Cl.[6] .............................. C12N 1/21; C12N 5/10; C12N 15/12; C12N 15/63

[52] U.S. Cl. .................................... 435/240.2; 435/252.3; 435/252.33; 435/254.2; 435/320.1; 536/23.5

[58] Field of Search ......................... 536/235; 435/320.1, 435/240.2, 252.33, 69.1, 252.3

[56] References Cited

U.S. PATENT DOCUMENTS 4,341,765 7/1982 Ruhenstroth-Bauer et al. ........... 514/2

OTHER PUBLICATIONS

Francavilla et al., Extraction and Partial Purification of a Hepatic Stimulatory Substance in Rats, Mice, Dogs, Cancer Research 47, Nov. 12, 1987, pp. 5600–5605.

Francavilla et al., Screening for Candidate Hepatic Growth Factors by Selective Portal Infusion after Canine Eck's Fistual Hepatology vol. 14, No. 4, Pt. 1, 1991, pp. 665–670.

Francavilla et al, Induction of Hepatocyte Stimulating Activity by $T_3$ and Appearance of the Activity depsite Inhibition of DNA Synthesis by Adrimaycin, Horm. metabol, Res. 16 (1984), pp. 237–242.

Francavilla et al., Further Steps of Hepatic Stimulatory Substance Purification, Digestive Diseases and Sciences, vol. 36, No. 5 (May 1991), pp. 674–680.

Francavilla et al., Liver Regeneration, Hepatic Simulatory Substance (HSS) In Liver Regeneration, 1993 AASLD Single Topic Symposium, Jun. 24–27, 1993.

Francavilla et al., The Effect of Hepatic Stimulatory Substance, Isolated from Regenerating Hepatic Cytosol, and 50,000 and 300,000 Substractions in Enhancing Survival in Experimental Acute Hepatic Failure in Rats Treated with D-Galactosamine, Hepatology, vol. 6, No. 6, 1986, pp. 1346–1351.

Starzl et al., The Origin, Hormonal Nature, And Action of Hepatotrophic Substances In Portal Venous Blood, Surgery, Gynecology & Obstetrics, Aug. 1973, vol. 137, pp. 179–199.

Starzl et al., Growth-Stimulating Factor In Regenerating Canine Liver, The Lancet, Jan. 20, 1979 vol. 1, No. 421, pp. 127–130.

Starzl et al., Reconstructive Problems In Canine Liver Homotransplantation With Special Reference To The Post-operative Role of Hepatic Venous Flow, Surgery, Gynecology & Obstetrics, Dec. 1960, pp. 733,–743.

Nakamura et al., Molecular cloning and expression of human hepatocyte growth factor, Nature, vol. 342, No. 6248, Nov. 1989, pp. 440–443.

(List continued on next page.)

*Primary Examiner*—Robert A. Wax
*Assistant Examiner*—Eric Grimes
*Attorney, Agent, or Firm*—Cushman Darby & Cushman

[57] ABSTRACT

A full-length cDNA clone has been isolated encoding a purified augmenter of liver regeneration (ALR) polypeptide prepared from the cytosol of livers from weanling rats. The 1.2 kb cDNA includes a 299 bp 5'-untranslated region, a 375 bp coding region and a 551 bp 3'-untranslated region. The cDNA encodes a protein consisting of 125 amino acids. The molecular weight of ALR calculated from the cDNA was 15,081 which is consistent with the size estimated by SDS-PAGE under reducing conditions. The molecular weight of the purified native ALR estimated by SDS-PAGE under non-reducing conditions is about 30,000, apparently with a homodimer structure. The recombinant ALR produced by expression of the cDNA in cultured cells was tested in vivo in the canine Eck's fistula model and found to have a potency equivalent to the purified native ALR. The most obvious immediate clinical use for the augmenter of liver regeneration is in the treatment of hepatic failure.

8 Claims, 11 Drawing Sheets

```
Met Arg Thr Gln Gln Lys Arg Asp Ile Lys Phe Arg Glu Asp Cys Pro
1               5                   10                  15

Gln Asp Arg Glu Glu Leu Gly Arg Asn Thr Trp Ala Phe Leu His Thr
            20                  25                  30

Leu Ala Ala Tyr Tyr Pro Asp Met Pro Thr Pro Glu Gln Gln Gln Asp
        35                  40                  45

Met Ala Gln Phe Ile His Ile Phe Ser Lys Phe Tyr Pro Cys Glu Glu
    50                  55                  60

Cys Ala Glu Asp Ile Arg Lys Arg Ile Asp Arg Ser Gln Pro Asp Thr
65                  70                  75                  80

Ser Thr Arg Val Ser Phe Ser Gln Trp Leu Cys Arg Leu His Asn Glu
                85                  90                  95

Val Asn Arg Lys Leu Gly Lys Pro Asp Phe Asp Cys Ser Arg Val Asp
            100                 105                 110

Glu Arg Trp Arg Asp Gly Trp Lys Asp Gly Ser Cys Asp
        115                 120                 125
```

OTHER PUBLICATIONS

Starzl et al., Effects of Insulin, Glucagon, And Insulin/Glucagon Infusions On Liver Morphology and Cell Division After Complete Portacaval Shunt In Dogs, The Lancet, Apr. 17, 1976, pp. 821–825.

Labrecque et al, Hepatology 7:100–106 (1987).

Yao et al., Chinese Med. J. 106:527–532 (1993).

Shima et al., Biochem. Biophys. Res. Comm. 180:1151–1158 (1991).

Labrecque, Dig. Dis. Sciences 36: 669–673 (1991).

Sambrook et al., *Molecular Cloning, A Laboratory Manual,* 2nd Edition, Cold Spring Harbor Lab. Press, Cold Spring Harbor, N.Y., 1989, pp. 11.1–11.19.

Hagiya et al., Proc. Natl. Acad. Sci. U.S.A. 91:8142–1846 (1994).

PUMP
F I-28
L
R
R.V.
I.V.C.
P.V.
PORTACAVAL SHUNT
BODY WALL
PERCENT LABELED HEPATOCYTES
0
4
8
12
16
C
2.5
5.0
10.0
20.0
40.0
ng/kg b.w./day

FIG. 5

```
Met Arg Thr Gln Gln Lys Arg Asp Ile Lys Phe Arg Glu Asp Cys Pro
1               5                   10                  15

Gln Asp Arg Glu Glu Leu Gly Arg Asn Thr Trp Ala Phe Leu His Thr
            20                  25                  30

Leu Ala Ala Tyr Tyr Pro Asp Met Pro Thr Pro Glu Gln Gln Gln Asp
        35                  40                  45

Met Ala Gln Phe Ile His Ile Phe Ser Lys Phe Tyr Pro Cys Glu Glu
    50                  55                  60

Cys Ala Glu Asp Ile Arg Lys Arg Ile Asp Arg Ser Gln Pro Asp Thr
65                  70                  75                  80

Ser Thr Arg Val Ser Phe Ser Gln Trp Leu Cys Arg Leu His Asn Glu
                85                  90                  95

Val Asn Arg Lys Leu Gly Lys Pro Asp Phe Asp Cys Ser Arg Val Asp
            100                 105                 110

Glu Arg Trp Arg Asp Gly Trp Lys Asp Gly Ser Cys Asp
        115                 120                 125
```

FIG. 6A

```
CGCGCGCTGG CGGTGGCATG CGCGCTGCTC TGTCCCGTCT CCTGCACGCC CTCTTGGCCC   60
CGCTGCTCGT ACGCCAGCAA TATGGCGGCG CCCAGCGAAC CCGCAGGTTT CCCTCGCGGC  120
AGTCGCTTCT CCTTCCTGCC GGGCGGCGCG CACTCGGAGA TGACCGACGA CCTGGTGACT  180
GACGCGCGGG GCCGCGGCGC AAGGCATAGA AAAGACAACG CCCCTGCCGC GGCCCCGGCG  240
CCGAAAGGTT TGGAGCACGG GAAGCACCGT GCCGGGCCTG CGTGGACTTC AAGTCGTGGA  300
TGCGGACCCA GCAGAAGCGG GACATCAAGT TTAGGGAGGA CTGTCCACAG GATCGGGAAG  360
AATTGGGTCG CAACACCTGG GCTTTCCTTC ATACGCTGGC CGCCTATTAC CCGGACATGC  420
CCACGCCAGA ACAACAGCAG GATATGGCCC AGTTCATACA TATATTTTCC AAGTTTTACC  480
CCTGTGAGGA GTGTGCAGAA GACATAAGGA AGAGGATAGA CAGGAGCCAG CCAGACACAA  540
GCACTCGAGT GTCCTTCAGC CAGTGGCTGT GCCGCCTTCA CAATGAAGTG AACCGGAAGC  600
TGGGCAAGCC TGATTTTGAC TGCTCAAGAG TTGATGAGCG ATGGCGTGAC GGCTGGAAGG  660
```

FIG. 6B

```
ACGGCTCCTG TGACTAAGGA TTACCACAGA CCGTGCAGGG CAACGCCGGG TTCTATGGGC   720
AACAGCCTGA CTGACGATTA AAGTGCATCT GAGCCAAAGC TTGTTTCTGT GGTGGGGGTG   780
GGATCCCCTA GAACACTGCC TATGGGAACC CTACCCACAG ACTCAGAAAC GGAGGTGCCC   840
ACTATAGACA GTTGGGTGGC TTCCTCAGGT CTTAAAGCCC CATGGGACTG AAGATGAGAG   900
GCAGGAGTGG TCCAGGGCAC CCCATACCCC TTATGATACC CATTATACAT TTGGGACATA   960
GTTGCCTCAA AGGAAGGTGG GCTAGACCAT TGCCTTCCTA CTACATATCC CCAGCTGCCT  1020
ACAGAACTGT GACCCAGGCA ACTCTGCCAT TTCAGAATTG AAGCAGGGTT CCAGCTCTAG  1080
TTGGGTTTTT CTCTTAGGGT AAACCAACCA TGGTGCCCAC TGTCAGCCTG GCACATGGTC  1140
TTCTGCAGCC AGGACAAACA TGTCAGCAGA GGATCCTGGG AAGGGCTTCC TTAGCGTTTG  1200
AGACCAAAAT AAAATGAAGT GACTT                                        1225
```

AUGMENTER OF LIVER REGENERATION (ALR)

BACKGROUND OF THE INVENTION

1. Field of the Invention

This invention relates to an augmenter of liver regeneration (designated as ALR), a novel polypeptide possessing a physiological activity enabling in vivo stimulation of DNA synthesis of hepatocytes, a nucleic acid molecule encoding for such polypeptide, recombinant expression vectors, transformants and methods for production of such polypeptide.

2. Description of the Related Art

Stage I: ORIGINAL RESEARCH AND DEVELOPMENT OF MODELS

The involvement of the inventors in the growth factor field dates back to the discovery in 1959 that consistently successful orthotopic liver transplantation (liver replacement) in mammals was not possible without providing normal portal venous inflow from the non-hepatic splanchnic organs (1). The reason for this was discovered in 1963 during further research to determine the optimal way to vascularize auxiliary (an extra organ as opposed to replacement) liver grafts for potential use in humans. The clinical objective was to provide a new liver without removing the diseased one, and therefore to leave the recipient with two livers. The dog experiments evaluating this possibility (FIG. 1, upper left) showed that the transplanted auxiliary liver allografts given portal inflow with systemic (vena caval) blood shrank to a fraction of their original size within a few days, even when there was no histopathologic evidence of immunologic rejection (2). However, this atrophy could be prevented if the allograft was nourished with normal portal venous blood, in which case the shrinkage afflicted the native liver that was deprived of this specific kind of blood (3). The results suggested that there were trophic (growth sustaining) substances in portal venous blood that were largely being removed by a single passage through the first liver to which they were exposed. To establish the validity of this conclusion, non-transplant models were developed in which the animal's own liver was divided into two fragments, differing only in the kind of blood flow delivered to the right and left main portal vein branches (4,5). In essence, this created two livers in the same animal (FIG. 1, upper right and lower left). The sizes of the hepatocytes in the differentially perfused liver fragments were measured with a morphometric technique that correlated well with the planimetric volume determination of single cells (FIG. 2). The results were expressed as size units (5).

In the first of these "double liver fragment" preparations (4), one part of the liver was given high volume venous inflow from the suprarenal inferior vena cava which delivered blood to the liver from the hind quarters and trunk (FIG. 1, upper right). The other liver portion was perfused by blood that drained in a normal way from the splanchnic organs into the portal vein. This was called "split transposition". The hepatocytes in the liver fragment vascularized with splanchnic venous blood became hypertrophic and had a 10-fold increase in basal replication. The hepatocytes in the liver portion nourished by vena caval return underwent atrophy and had only a three-fold increase in basal replication. These changes in the fragment deprived of portal blood were indistinguishable from those caused in the whole liver by simple Eck's fistula (4–6). However, the total liver mass of the combined sides always remained the same as a normal whole liver suggesting that the size adjustments involved humorally-mediated "cross talk" between the two sides, suggestive of a growth factor or factors. Biochemical end points in the two liver fragments (5) showed that the two liver fragments apparently existed in different chemical environments that were dictated largely by the presence or absence of insulin.

Similar striking disparities between the two liver fragments were observed when the natural portal venous blood was divided between them in what became known as the splanchnic division model (FIG. 1, lower left). Hepatocytes exposed directly to the venous effluent from the upper abdominal organs (pancreas, stomach, duodenum, and spleen) were hypertrophic (as in FIG. 2, right) and hyperplastic while those in the fragment nourished by the nutrient-rich intestinal venous return developed the same kind of changes seen in conventional Eck's fistula livers (5–7).

In the most discriminating of all double liver fragment models, and the one that allowed the invention of this patent application to proceed, a completely diverting portacaval shunt (Eck's fistula) was constructed, followed by the continuous infusion of insulin or other test substances into the right or left portal vein branch (FIG. 1, lower right). The result of this reconstructive surgery was the ability to directly compare the effect on the infused liver fragment with the non-infused side serving as a control. When insulin was given, the treated side was spared almost completely from the hepatocyte atrophy and organelle disruption characteristic of Eck's fistula (Table 1) and also exhibited the same 10-fold increase in cell renewal (Table 2) (8,9) we had attributed from previous circumstantial evidence to endogenous insulin in the split transposition and splanchnic division models. These hypertrophic and hyperplastic effects, for which we coined the term "hepatotrophic" were not found on the untreated side, further confirming the specificity of the effect and the high degree of first pass consumption of the hormone (insulin) by the liver. This direct evidence that insulin was a growth factor completed the first stage of the discovery process leading to the present patent application.

Stage II: THE SEARCH FOR NON-INSULIN HEPATOTROPHIC FACTORS

Other Hormones—An early hypothesis stemming from the foregoing observations was that liver growth including regeneration was modulated by the interactions of multiple hormones of splanchnic and non-splanchnic origin (5, 10–18). This trail turned cold when other hormones could not be added, in the ensuing 15 years, to the list started by insulin, except for the weakly hepatotrophic thyroxin $T_3$ (19). This intensified the search for non-hormonal growth factors. However, this search became dependent in the 1970s and 1980s on primary culture of adult rat hepatocytes as a screening bioassay (20,21), with a few notable exceptions including our continued use of the Eck's fistula in vivo model (9,19,22).

The Non-Hormonal Growth Factor—Forty years ago, Teir and Ravanti (23) and Blomqvist (24) summarized earlier work by others and reported evidence of their own that a growth stimulatory factor was present in a cell mash prepared from regenerating livers after partial hepatectomy in adult rats, and in hyperplastic weanling livers. The idea faded until 1975 when LaBreque and Pesch (25) prepared a crude cytosol from regenerating livers which augmented the normally modest regeneration response of naive (previously unaltered) rats after 34% hepatectomy when it was given intraperitoneally. We confirmed these results in canine experiments when the active cytosol was infused intraportally (26).

More importantly, the cytosol also was found to have the same hepatotrophic effects as insulin when tested with the in vivo canine Eck's fistula infusion model (22). Cytosol prepared from the livers of sham operated dogs or from the residual liver fragment of the cytosol donor one day after 70% hepatectomy was inert. However, it was hepatotrophic if the fragments were harvested two and three days post-resection at the time when hepatic regeneration in dogs is known to be maximal (27).

This "X-factor", which originally was called hepatic stimulatory substance (HSS) and more recently augmenter of liver regeneration (ALR), was not mitogenic when purified fractions were tested on cultured hepatocytes (28,29). However, throughout the steps toward its million times purification from rat liver, amino acid sequencing, and production with recombinant gene technology (this patent application), its biologic activity could be tracked by testing with the in vivo canine Eck's fistula infusion model (19,28, 29).

During the difficult Stage II development, we showed that the crude cytosol was active only if the liver of the animal injected with it already was in heightened mitosis, a condition that was present in our Eck's fistula assay in which stable heightened cell renewal is characteristic. Although we turned throughout the 1980s to the rat as a source of ALR, this in vivo assay in dogs permitted decisive identification of progressively purified fractions from rat liver.

SUMMARY OF THE INVENTION

The present invention discloses the isolation and purification of augmenter of liver regeneration (ALR) using both the canine in vivo Eck's fistula assay and the partially hepatectomized rodent assay. The molecular weight of the purified rat ALR protein was determined to be 15,000 in the reduced form and 30,000 in the non-reduced form, indicating that ALR is a homodimer in its native state. Both determinations were made with SDS-PAGE.

The present invention further discloses the isolation of a full-length cDNA clone encoding a purified augmenter of liver regeneration protein prepared from the cytosol of livers from weanling rats. The full-length clone is a 1.2 kb cDNA containing a 299 bp 5'-untranslated region, a 375 bp coding region and a 551 bp 3'-untranslated region. The complete nucleotide sequence for the cDNA is given in SEQ ID NO:1. The molecular weight of the ALR protein, as estimated from the deduced amino acid sequence (SEQ ID NO:2), is 15,081. This molecular weight estimate is consistent with the molecular weight estimate of the native protein determined by SDS-PAGE under reducing conditions.

The present invention further discloses the preparation of recombinant expression vectors with exogenous DNA encoding the ALR and the transformation of both prokaryotic and eukaryotic cell lines with the recombinant expression vectors. Such transformed cells are capable of producing recombinant ALR in culture and the recombinant ALR is of equivalent potency to the purified native ALR when tested in the canine in vivo Eck's fistula model.

BRIEF DESCRIPTION OF THE DRAWINGS

FIG. 5 is the deduced amino acid sequence for rat ALR. This sequence corresponds to SEQ ID NO:2.

FIG. 6 is the entire 1225 nucleotide sequence for the ALR cDNA. This sequence corresponds to SEQ ID NO:1.

DETAILED DESCRIPTION OF THE INVENTION

Figure 1:
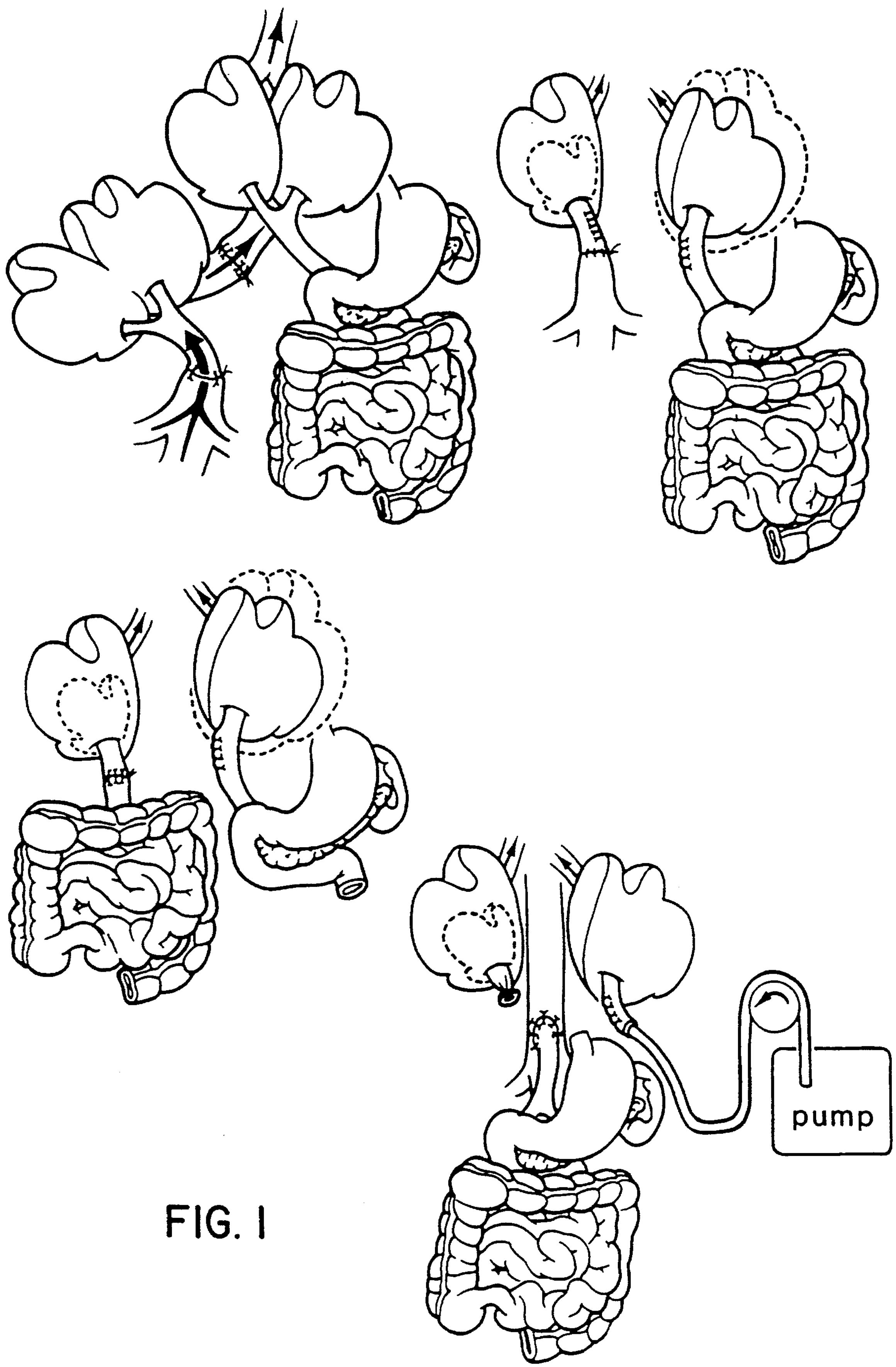
FIG. 1 shows liver operations which illustrate the effect of portal blood on liver growth and trophism.
Figure 2:
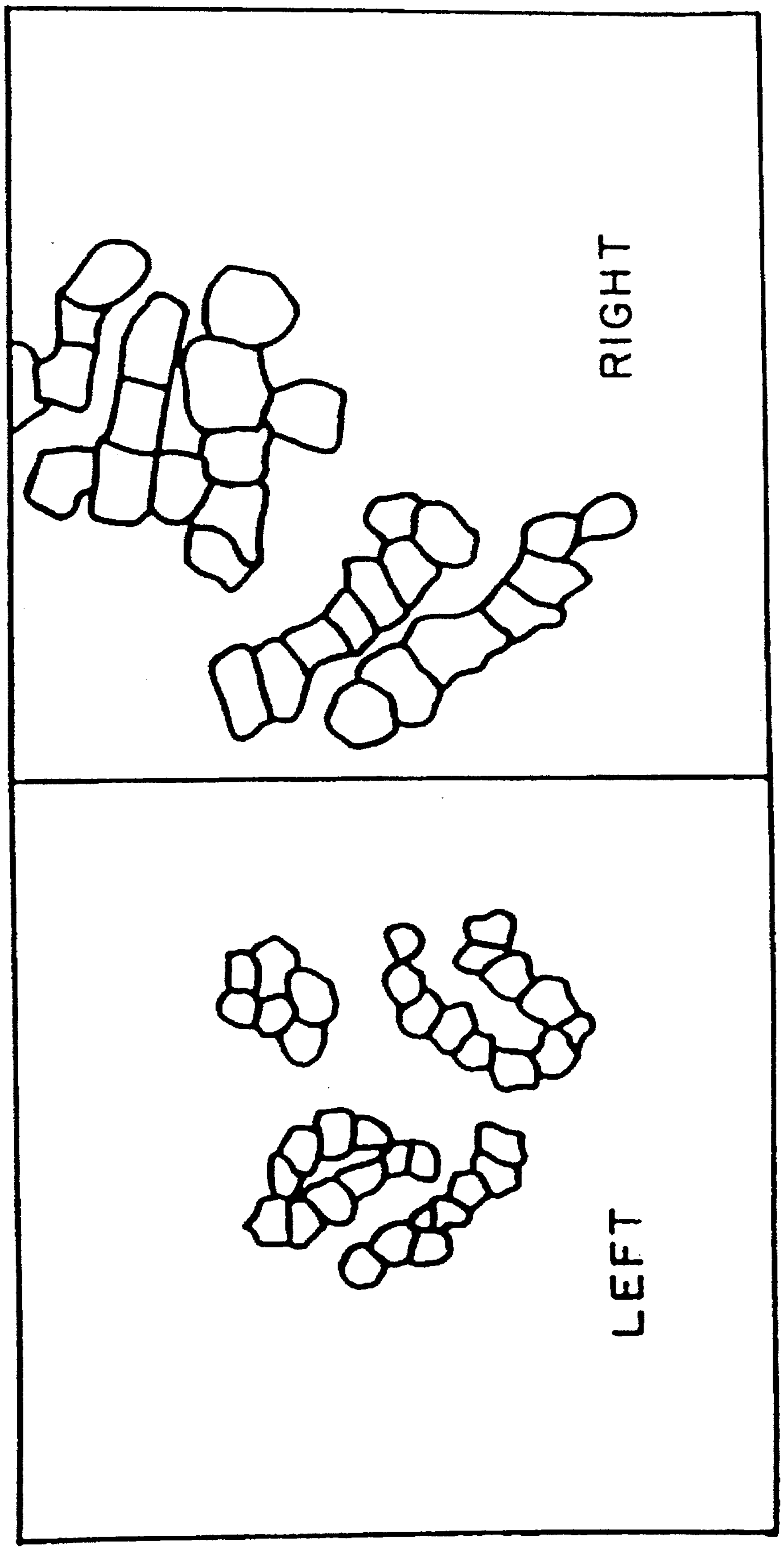
FIG. 2 depicts hepatic shadows traced during histopathological examinations cut on on standard paper and weighed as an index of hepatocyte size (5). The left side of the figure shows traced hepatocytes from a liver section that had a venal caval or intestinal blood supply while the right side shows traced hepatocytes from a liver section that had a splanchic blood supply.

The substance which once was called hepatic stimulatory substance (HSS) and now referred to as augmenter of liver regeneration (ALR) was extracted from the livers of weanling rats (whose livers were hyperplastic), purified to a 30 kDa fraction using various chromatographic techniques, native SDS and reducing PAGE and immunoblotting with specific monoclonal antibody. The activity of the purified ALR was assayed at each step with the in vivo canine Eck's fistula model, also known as the dog portacaval shunt assay. This new growth factor belongs to a physiologic family of liver growth factors of which the first identified was insulin. However, ALR has no homology to insulin or any other known growth factor.

The biochemical steps of ALR purification from the weaning rat liver are as follows:

| | | Product |
|---|---|---|
| 1. | Remove the liver, immediately after killing by guillotine, between 7:00 and 8:00 am. | |
| 2. | Mince and then homogenize the liver in 150 mM sodium acetate buffer, pH 4.65 (35:100 w/v). | |
| 3. | Ultracentrifuge homogenate at 24,000 xg for 30 min at 4° C. | Cytosol fraction (Cyt-F) |
| 4. | Heat at 65° C. for 15 min. | |
| 5. | Centrifuge at 30,000 xg for 20 min at 4° C., collect supernatant and add to it 6 vol of cold ethanol (1:6, v/v). | |
| 6. | Stir at 2–8° C. for 2 hr. | |
| 7. | Centrifuge at 30,000 xg for 20 min at 4° C. | |
| 8. | Resuspend precipitate in 0.150 mM ammonium acetate, pH = 6. | Alcohol fraction (OH—F) |

-continued

| | | Product |
|---|---|---|
| 9. | Filter OH—F through an Amicon membrane with a molecular weight cutoff of 30,000 Da. | |
| 10. | Collect the filtrate and concentrate it by a 500-Da cutoff Amicon membrane. | Mr 30,000 fraction (30 kDa-F) |
| 11. | Lyophilize 30 kDa-F. | |
| 12. | Resuspend lyophilized 30 kDa-F in phosphate buffer 5 mM, pH 6, and perform chromatography using mono Q HR 5/5 column with a linear 0–2000 mM NaCl gradient in phosphate buffer. | |
| 13. | Collect the chromatographic peak. | 150 fraction ($F_{150}$) |

In our first experiments, the activity of each fraction was assayed in vivo with the rat or mouse 40% partial hepatectomy model, similar to the hepatectomy assays originally used by LaBreque and Pesch in rats and by us in dogs (26). Briefly, a heightened background of DNA synthetic activity in vivo was induced in host rats and mice by a 40% partial hepatectomy. Six hours after the partial hepatectomy, rats were given i.p. injections of two ml of various extracts at protein concentrations as indicated in Table 3. Seventeen hours later, 50 μCi [$^3$H]thymidine were injected i.p. and the animals were sacrificed one hour later.

Extracts (0.2 ml volume) were also administered i.p. to mice at 30 hours after 40% partial hepatectomy and DNA synthesis was studied 18 hours later. [$^3$H]thymidine (10 μCi/mouse) was injected i.p. one hour before sacrifice (i.e., 47 hours following partial hepatectomy). Nonhepatectomized rats received injections of extracts 24 and 18 hours before determination of [$^3$H]thymidine incorporation, and mice received injections at 48, 24 and 18 hours. [$^3$H] thymidine incorporation, labeling and mitotic indexes were determined as previously described (22). An augmentation of all three parameters, beyond the modest response that is usually present in 40% PH or in unoperated animals was considered to be indicative of a proliferative inducing activity of the liver extracts (29).

Table 3 shows the results expressed as augmented DNA synthesis versus the degree of purification. However, this assay was too imprecise to permit demonstration of a statistically significant effect. Further purification beyond fraction 150 was obtained through the use of nondisassociating polyacrylamide gel electrophoresis and the use of specific monoclonal antibody (28). An aliquot of 0.6 mg lyophilized fraction $F_{150}$ resuspended in Tris buffer, 0.025M, pH 8.3, underwent electrophoresis using nondisassociating PAGE (28,29) on 8% acrylamide. With this technique, $F_{150}$ generates several distinct bands and the gel can be divided into four discrete zones from which the proteins can be eluted. The resulting eluates, acrylamide fractions 1–4 ($AcrF_1$–$F_4$), were dialyzed against 150 mM ammonium acetate, lyophilized, and stored at −70° C. until being tested further. This was the last fraction assayed by the rat hepatectomy model (Table 3).

In addition to this progress in purification, we turned to the in vivo canine Eck's fistula model as our standard assay, using the partial hepatectomy rat model only sporadically for spot checks. For the definitive assay, i.e., the Eck's fistula model, conditioned female beagle dogs weighing 8.3 to 13 kg were anesthetized with intravenous sodium pentobarbital, halothane and nitrous oxide. Side-to-side portacaval shunt was performed and converted to a functional end-to-side shunt by ligation of the portal vein above the anastomosis (FIG. 1, lower right). The main right and left portal veins were isolated, and the right vein was ligated. The left portal branch was cannulated with a 2.4 mm (internal diameter) cannula that was advanced for one cm, secured and led through the abdominal wall (Cormed II AIF, Cormed Inc., Murray Hill, N.J.) that was incorporated into a nonrestricting light body cast. Test substances dissolved in saline modified by the addition of 5 mmol/L ammonium acetate and 5 mg/L BSA (to avoid aggregation on the plastic tubing) were infused continuously at 25 ml/day for 4 days beginning promptly after completion of the portacaval shunt. For positive controls, the classical insulin experiments were always repeated. For negative controls, it was established that the vehicle was inert. The animals were given a sugar water diet ad libitum on the day of the operation and a regular diet thereafter. Before the animals were killed, hepatic and kidney function tests were obtained. Rises in serum creatinine or bilirubin or falls in serum albumin were not seen. Minor increases in serum transaminase and alkaline phosphatase typical of Eck's fistula (7) were common. All dogs were active, ate normally and appeared clinically well.

Pathological and Cytological End Points

The pathological and cytological end points measured were the same as in the previous growth factor research (8,9,19,22). Four days after portacavalshunt, 0.2 mCi/kg of intravenous [$^3$H]thymidine was given with a specific activity of 80 to 90 Ci/mmol (Dupont New England Nuclear Research Products, Boston, Mass.). Two hours later, while the dogs were under sodium pentobarbital anesthesia, specimens were taken from left and right lobes of the liver and fixed in 10% normal buffered formalin. The dogs were killed with an intravenous bolus of potassium chloride. The patency of the anastomosis and the correct position of the catheter tip were confirmed.

The liver tissue was processed and stained with hematoxylin and eosin. Autoradiography was carried out with Kodak NTB2 liquid emulsion (Eastman Kodak, Rochester, N.Y.) with an exposure time of at least 30 days. The number of replicating hepatocytes as an index of hepatocyte regeneration was determine by counting the number of [$^3$H] thymidine-labeled nuclei per 1,000 hepatocytes. The size of individual hepatocytes (index of hypertrophy or atrophy) was determined by tracing out at least 500 midzonal liver cells projected on standard thickness paper, cutting out the individual silhouettes and weighing each (5,8,9,22). This method has been shown to be accurate for determining hepatocyte cell size and has been validated by planimetry and studies of unicellular organisms, the size of which has been determined directly (5).

In normal, unaltered dogs 1.5±0.5 (S.D.) labeled hepatocytes per 1,000 hepatocytes are present in the liver, with the size of midzonal hepatocytes being 0.16±0.01 (S.D.) size units. After Eck's fistula, the replication rate is nearly tripled (8,9,19,22), and the hepatocyte size is almost halved within four days (8,9,19,22), after which a stable state exists (6,30). The exceptional reproducibility of these changes makes it easy to determine the effects of active growth factors on this transformation. Growth factors prevent the atrophy and increase further the already heightened cell renewal. Each experiment serves as its own control because the cell replication and size in the directly infused liver lobes can be compared with these measures in the contralateral uninfused lobes.

When acrylamide fraction 4, Acr-$F_4$, was administered as a continuous left portal vein infusion beginning six hr after portacaval shunt, the mitotic rate tripled in the left liver lobe while no effect was seen in the right side of the liver. This effect was completely eliminated with the addition of anti-Acr-$F_4$ monoclonal antibody (28) to the infusion fluid (see Table 4 for comparable results). The monoclonal antibody vehicle was inert when tested alone.

Determination of Rat ALR Amino Acid Sequences

Figure 3:
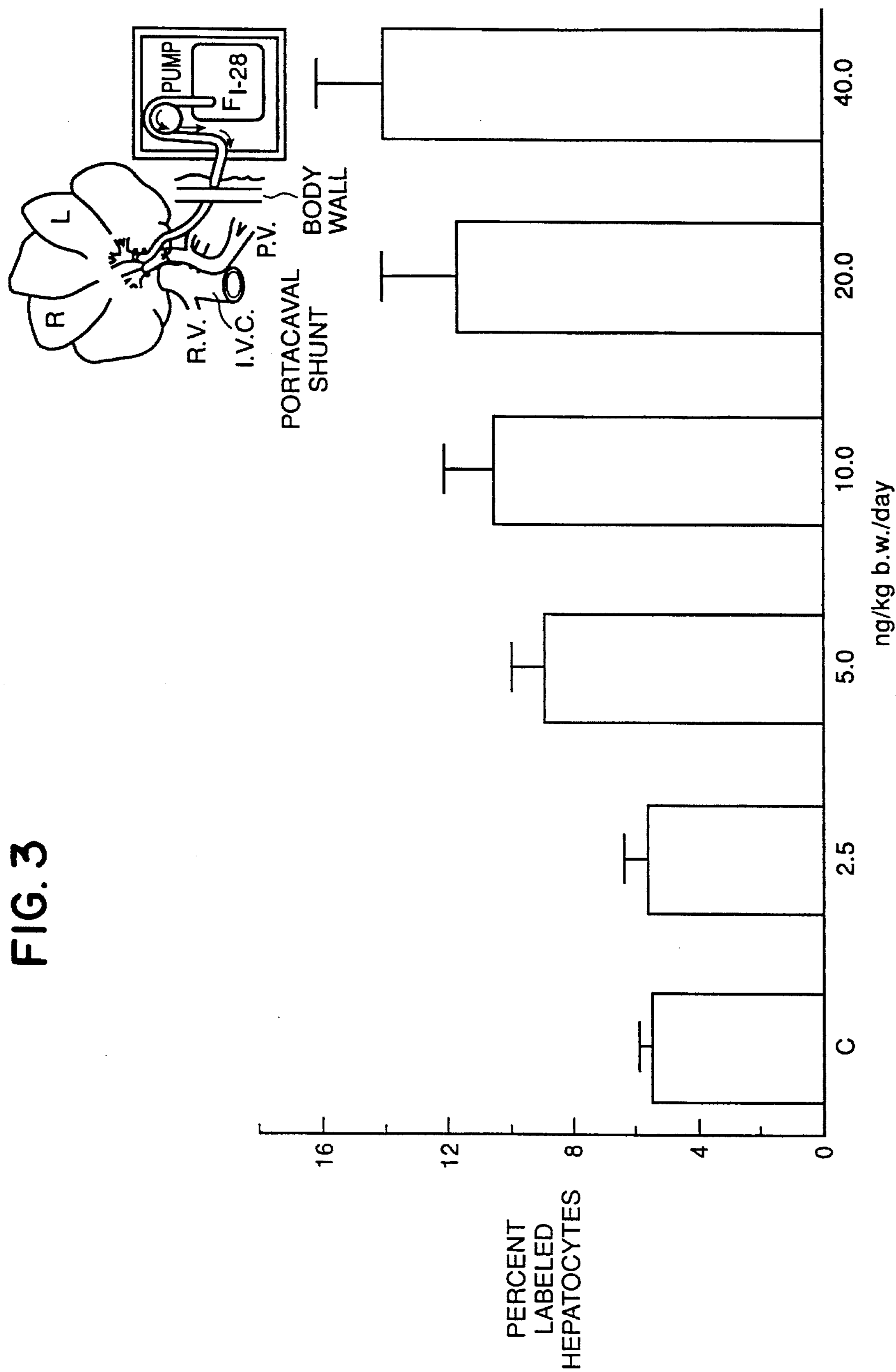
FIG. 3 demonstrates a dose-reponse effect on liver proliferation of the 30 kDa band infused in the left lobe of dogs with portacaval shunt (PCS).

200 μg of Acr-$F_4$ were separated by SDS PAGE. Four bands were identified and tested in the dog portacaval shunt model. The 30 kDa band was found to be active. FIG. 3 shows the activity and dose response curve for the 30 kDa band. To determine the amino acid sequence, the gel was stained with Coomassie Brilliant Blue, and the 30 kDa band was sliced, homogenized with 150 μl of buffer (0.1M Tris-HCl [pH 9.5], 0.3% SDS) and incubated at 37° C. for 18 hr. The sample was filtered through a 0.22 μm filter (Ultrafree-C3GV, Millipore) and the filter was washed once with 100 μl of the same buffer. A total of 250 μl of 30 kDa filtrate was further purified by Phenyl-5PW RP column chromatography (4.6×75 mm TOSOH) equilibrated with 0.1% TFA (trifluoroacetic acid [V/V%]). The 30 kDa band was eluted with the solvent mixture of isopropanol and acetonitrile (1:1) containing 0.1% TFA and eluted at a concentration gradient of 40%. The peak was collected, lyophilized and combined with 200 μl of 50 mM Tris-HC1 buffer (pH 9.5) and incubated with 1 μg of *Achromobacter liticus* protease I (EC 3.4.21.50) at 37° C. for 15 hr. The digested peptides were then eluted from an ODS chromatography column (AP-302, S-530, 4.6×150 mm YMC) which had been equilibrated with 0.1% TFA. The elution agent was a 1:1 mixture of isopropanol with acetonitrile (containing 0.1% TFA). A linear gradient was run from 0 to 80% (a 0 to 80% gradient of a 1:1 mixture of isopropanol with acetonitrile).

The amino acid sequence was determined from the N-terminus of each peak by Edman degradation with Protein Sequencer 477A and Analyzer 120 A (Applied Biosystems Co).

The following amino acid sequences were obtained:*

*At this point, the "Xaa" amino acids had not yet been identified. These have been identified subsequently (see SEQ ID NO:2).

ALR-19 Phe-Tyr-Pro-Xaa-Glu-Glu-Xaa-Ala-Glu-Asp-Ile (SEQ ID NO:4)

ALR-20 Leu-Gly-Lys-Pro-Asp-Phe-Asp-Xaa-Ser-Xaa-Val (SEQ ID NO:5)

ALR-26 Xaa-Ile-Asp-Arg-Ser-Gln-Pro-Asp-Thr-Ser-Thr-Arg-Val-Ser-Phe-Xaa-Gln-Xaa-Leu-Xaa-Xaa-Leu (SEQ ID NO:6)

All three sequences have no homology with known sequences in the Protein Identification Resource (PIR) R34.0 data bank as of September 1992.

Isolation of cDNA Clones

Isolation of mRNA

Total cellular RNA was isolated from the livers of two week old Fischer rats using the guanidine isothiocyanate procedure of Chomczynski et al. (31). Three mg of RNA were isolated from one gram of liver and then resuspended in 500 μl elution buffer (10 mM Tris-HCl, [pH 7.5], 1 mM EDTA, 0.1% SDS) and mixed with 500 μl of Oligotex-dT30 (Japan Roche Company). The mixture was heated for 5 minutes at 65° C. and then chilled on ice. 1/10 volume of 5M NaC1 was added and incubated for 5 minutes at 37° C. mRNA was precipitated with Oligotex after spinning for 5 minutes at 10,000 xg. Elution buffer was added to the precipitate and the solution was vortexed and heated for 5 minutes at 65° C. mRNA was recovered in the supernatant after spinning for 5 minutes at 10,000 xg. The above procedure yielded about 15 μg of mRNA.

B) Preparation of cDNA Library cDNA was prepared from 5 μg mRNA obtained by procedure (A) using the cDNA synthesis system (Amersham) and ligated into a λ-gtll vector with EcoRI adapters and packaged using the cDNA cloning system (Amersham). In all, approximately $1\times10^9$ recombinant phages were generated.

c) Screening of cDNA Library

The rat ALR cDNA was isolated in three stages. First, single-stranded cDNA prepared from two week old rat livers was amplified by PCR with degenerated oligonucleotide primers based on the partial amino acid sequence. Next, the PCR product was sequenced to confirm the primer sequence in the insert (32). Finally, PCR product was used to screen the cDNA library.

C-1 Single Stranded aDNA Synthesis

Single-stranded cDNA was synthesized from liver mRNA primed with the oligodeoxynucleotide, 5'-AACTGGAA-GAATTCGCGGCCGCAGGAA($T_{18}$)-3' (SEQ ID NO:7) which is complementary to the poly(A) tail of mRNA and includes a Not I restriction site, using first strand cDNA synthesis kit (Pharmacia).

C-2 PCR

Single-stranded cDNA was amplified by PCR with a mixture of 5' primers:

5'-ATIGA(T/C)CGIAG(T/C)CA(A/G)CCIGA(T/C)AC-3' (SEQ ID NO:8),

5'-ATIGA(T/C)CGITCICA(A/G)CCIGA(T/C)AC-3' (SEQ ID NO:9),

5'-ATIGA(T/C)AG(A/G)AG(T/C)CA(A/G)CCIGA(T/C)AC-3' (SEQ ID NO:10) and

5'-ATIGA (T/C)AG(A/G)TCICA(A/G)CCIGA(T/C)AC-3' (SEQ ID NO:11), (wherein I is inosine).

These primers include sequences of all possible codons specifying amino acid sequence Ile-Asp-Arg-Ser-Gln-Pro-Asp-Thr of ALR 26 (SEQ ID NO:12) and 3' primer, 5'-GC-CGCAGGAA$(T)_{10}$-3' (SEQ ID NO:13) with 4 mM of each primer in 80 mM KCl, 1.5 mM $MgCl_2$, 10 mM Tris-HCl (pH 8.8), 500 μg/ml BSA, 0.1% sodium cholate, 0.1% Triton X-100, 200 μM deoxynucleotide triphosphate (dNTP), and 1 unit of Tth DNA polymerase (Toyobo) in 100 μl of reaction mixture. The PCR was performed under the following conditions: 95° C. for 1 minute, 58° C. for 28 minutes, 75° C. for 3 minutes per cycle for 40 cycles. The PCR products were analyzed by agarose gel (1.2%). A 360 bp fragment was isolated from a gel, subcloned in EcoRV sites of pBluescript by TA cloning (33) and sequenced by the dideoxy method (32) with Sequenase (United States Biochemical Company). Insert fragment cloned in pBluescript was cut with SalI and XbaI, separated and extracted from the gel. PC-ALR 26–24 subclone was selected for screening for the cDNA library.

C-3) eDNA Screening by Plaque Hybridization

The hybridization was performed by standard procedure (34).

The PCR probe obtained (C-2) was labelled with ($\alpha$-$^{32}$P) dCTP by the multiprimed DNA labelling system (Amersham). After hybridization, the filters were withdrawn from the solution, washed with 0.9M NaCl/0.09M sodium citrate at 65° C. four times. The filters were air-dried and autoradiographed at 70° C. for one day on an X-ray film using the intensifying screen. After developing the film, the plaques corresponding to the signal region were scraped off from the master plate. The above procedure was repeated to purify the plaques having a positive signal. Four positive clones were eventually isolated.

D) Structural Analysis of the cDNA Clone

Figure 4:
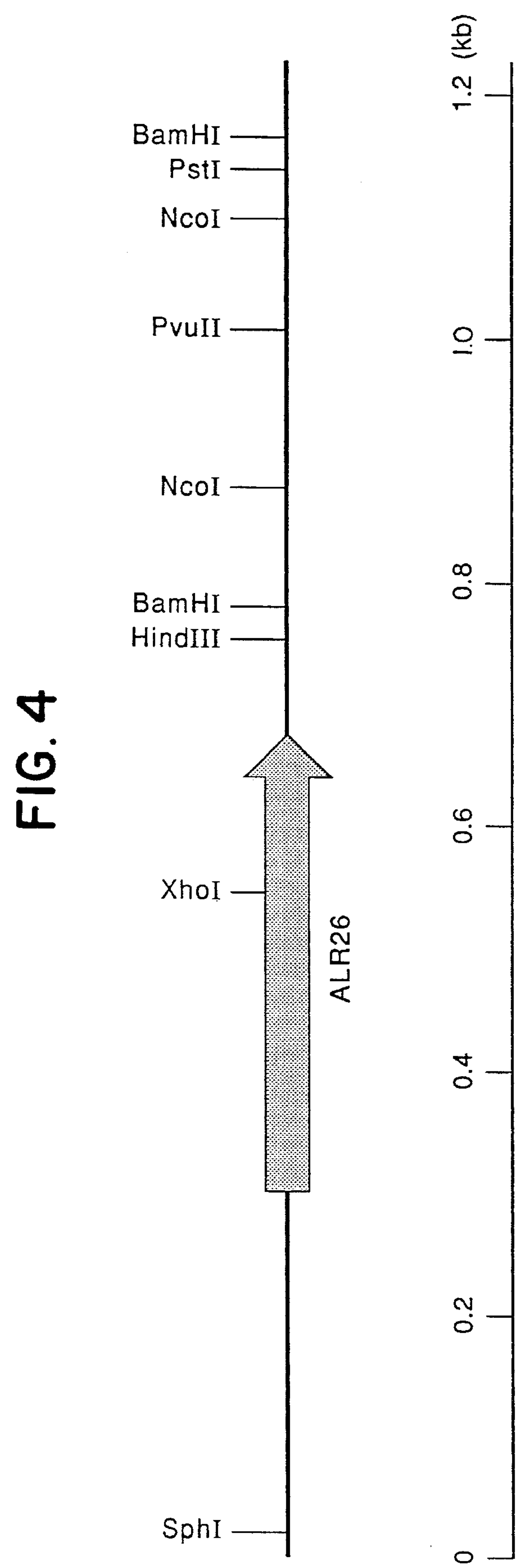
FIG. 4 is a schematic representation of the rat ALR cDNA showing the location of various restriction sites.

ALR-26-5 cDNA was digested with EcoRI and ligated in pBluescript. The resultant plasmid was further analyzed by restriction enzyme digestion and sequencing. As seen in FIG. 4 and SEQ ID NO:1, rat ALR cDNA is about 1.2 kb in entire length. When the cDNA of ALR 26-5 was searched for the longest open reading frame, the translation initiation codon (ATG) of rat ALR was presumed to start at nucleotide (nt) 300 and terminate (TAA) at nt 675 (SEQ ID NO:3). FIG. 5 shows the deduced amino acid sequence (SEQ ID NO:2) from the cDNA sequence (SEQ ID NO:3 and FIG. 6). The region corresponding to the amino acid sequences of the peptides derived from ALR-19, ALR-20, and ALR-26 are underlined and this indicates that the cDNA of ALR-26-5 is the cDNA coding for rat ALR protein. These results show that the coding size is 375 nucleotides long and code for a protein made of 125 amino acids with a calculated molecular weight of 15,081. The estimated molecular weight by SDS-PAGE of the purified native ALR from the liver of a weanling rat was 30 kDa under non-reducing conditions and 15 kDa under the reducing conditions.

It is presumed that the native form of ALR is a homodimer. Also ALR does not contain an N-linked glycosylation site. ALR is a novel protein. In Gene Bank R74.0, as of December 1992, ALR's only homology (50%) is with yeast nuclear gene ERV1, which is involved in oxidative phosphorylation and vegetative growth and is essential for yeast life (35).

Preparation of Recombinant ALR by COS Cells, *E. coli*, and *S. cerevisiae*

A. Construction of COS cell expression vector CDMmcs-dALR26

Figure 7:
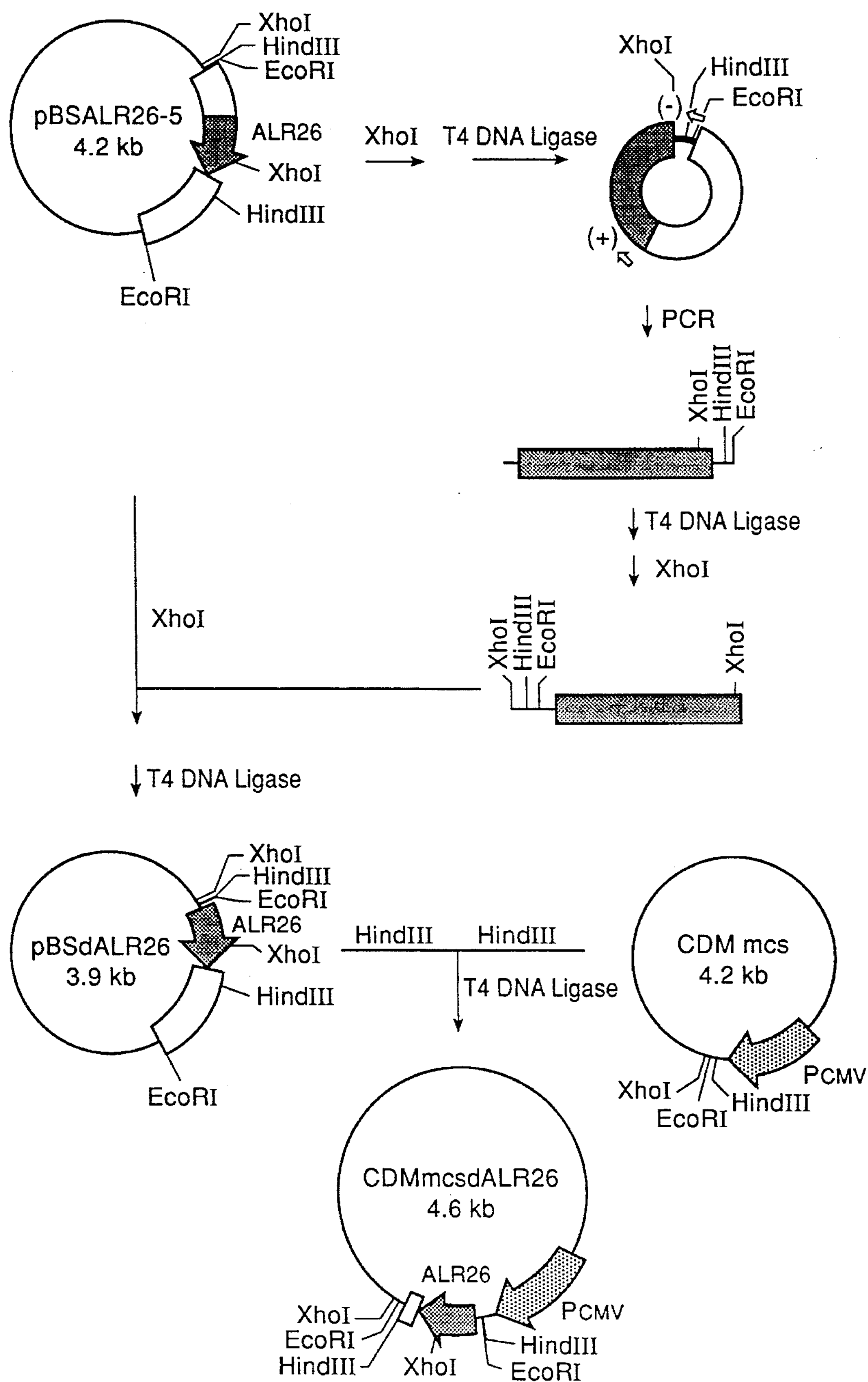
FIG. 7 is a schematic representation of the prepartion of vector CDMmcsdALR26 used to infect COS-1 cells.

To express the cloned cDNA ALR-26-5 in COS cells and ensure the ALR activity, an expression vector was constructed as follows. The highly G-C rich 5'-untranslated region of the ALR cDNA was eliminated by the PCR-based in vitro mutagenesis technique (42). The 1.2 kb EcoRI DNA fragment of the phage clone ALR-26-5 was inserted into the EcoRI site of pBluescript SK+ (Stratagene). The plasmid DNA of the subclone designated as pBSALR26-5 was digested with XhoI and self-ligated with T4 DNA ligase and then used as the template for the PCR. This step was necessary to shorten the length of the cDNA to be amplified. PCR was carried out using the thermostable Pfu DNA polymerase (Stratagene) and synthetic primers 5'-TGGACTTCAAGTCGTGGATG-3' (SEQ ID NO:14) and 5'-GAATTCGATATCAAGCTTATCG-3' (SEQ ID NO:15) which were based on the nucleotide sequences around the translation initiation codon of ALR-26 and the multiple cloning site of pBluescript SK+, respectively. The PCR product was self-ligated, digested with XhoI and then used to replace the XhoI fragment of pBSALR26-5, generating plasmid pBSdALR26. The expression vector CDMmcs (36) is a derivative of CDM (37) whose HindIII-XbaI fragment which included the stuffer sequence of the cloning sites has been replaced with the HindIII-XbaI multiple cloning site of Rc/RSC (Invitrogen). The 0.5 kb HindIII fragment of pBSdALR26 was inserted into the HindIII site of CDMmcs which is located downstream of the cytomegalovirus promoter. The expression vector CDMmcsdALR26 was finally obtained (FIG. 7) and used to transfeet the COS cells.

COS-1 cells (ATCC CRL-1650) were transfected with CDMmcsdALR26 by the DEAE-dextran method (38) and tested for the production of r-ALR by the following procedure. COS-1 cells were first suspended to a concentration of about $1\times10^6$ cells/ml in DMEM (Nissui Co.) with 10% FCS. Two ml of the suspension were placed into each well of a 60 mm dish and incubated overnight at 37° C. in a $CO_2$ incubator. Subsequently, the medium was removed and the cells were washed with DMEM twice. Two ml of DMEM containing 50 mM Tris-HCl (pH 7.4) and 400 μg/ml DEAE-dextran (Pharmacia) containing two μg of CDMmcsdALR26 were added to the cells and the mixture was allowed to stand in a $CO_2$ incubator for 12 hr. The media was removed from the cells and the cells were washed with DMEM (without FCS) twice. Two ml of DMEM (without FCS) was added to the plate and the cells were scraped from the plate, homogenized, and then centrifuged at 1600 xg for five minutes to get the cytosolic fraction. Both the culture medium and cytosolic fraction were assayed for in vivo thymidine uptake activity in hepatocytes in the dog portacaval shunt assay. The results are shown in Table 4. ALR activity was observed only in the cytosolic fraction.

B. Construction of *E. coli* Expression Vector pKKdALR26

Figure 8:
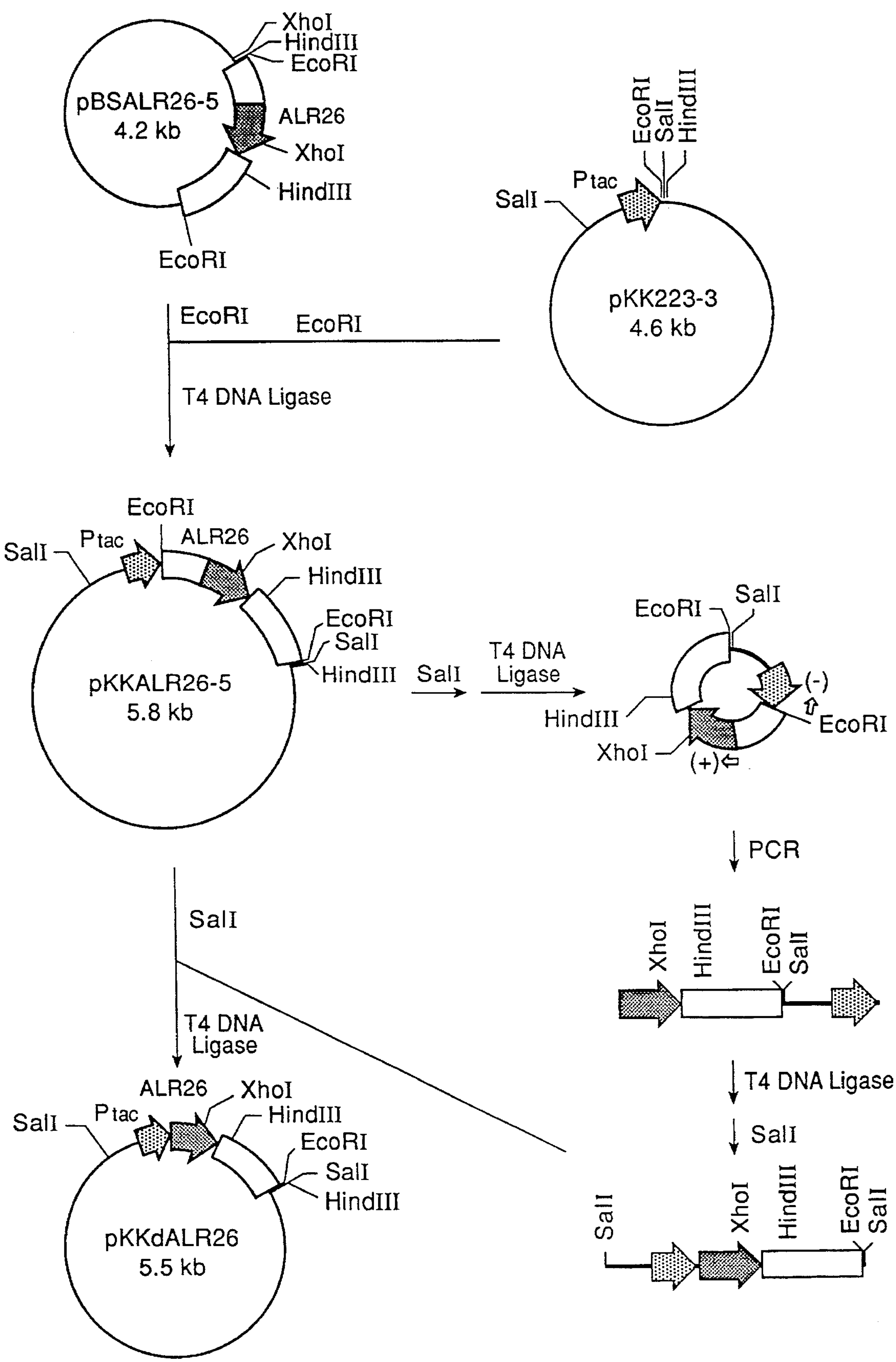
FIG. 8 is a schematic representation of the preparation of plasmid pKKALR26 used to express ALR cDNA in *E. coli.*

To express the cloned cDNA ALR26-5 in *E. coli* cells and obtain the gene product, an expression vector was constructed as follows. The protein coding sequence of the ALR26-5 cDNA was inserted just downstream of the translational initiation signal of the expression vector pKK223-3 (Pharmacia) using the PCR based in vitro mutagenesis technique as described for COS, the mammalian expression vector (see Section A, above). The EcoRI fragment of ALR26-5 cDNA was inserted into the EcoRI site which is located downstream of the tac promoter and ribosome-binding site, then generating the plasmid pKKALR26-5. The plasmid DNA of pKKALR26-5 was digested with SalI and then self-ligated to provide the template for the PCR. PCR was carried out with Pfu DNA polymerase (Stratagene) and synthetic primers 5'-ATGCGGACCCAGCAGAAG-3' (SEQ ID NO:16) and 5'-ATTCTGTTTTCCTGTGTGAAATT-3' (SEQ ID NO:17) which were based on the nucleotide sequences around the translational initiation codon of ALR26-5 and the transcription/translation regulatory region of pKK223-3, respectively. The PCR was self-ligated and digested with SalI, then used to replace the SalI fragment of pKKALR26-5. The resulting plasmid pKKdALR26 (FIG. 8) was used to express the ALR cDNA in *E. coli.*

*E. coli* JM109 cells were transfected with *E. coli* expression plasmid pKKdALR26 obtained above by the standard $CaCl_2$-phosphate-transformation method. The transformant was inoculated in five ml LB and incubated overnight. 500 μl of the culture was inoculated in 50 ml LB medium for 2.5 hr. One mg IPTG (isopropyl-D-thiogalactopyranoside, Sigma) was added to the culture and incubated another six hours. The cells were precipitated by centrifugation at 3,000 xg for 10 minutes. Cells were resuspended in five ml of 10 mM PBS (pH 7.0) and five mg/ml lysozyme (Sigma) was added and the suspension was incubated for 30 minutes at room temperature. After incubation, the suspension was sonicated for two minutes at full scale. The sonicated cell suspension was centrifuged at 7,000 xg for 15 minutes. The supernatant was subsequently applied on a Mono Q ion exchange column and eluted with a linear 0–300 mM NaCl gradient. The 150 mM NaCl eluate was collected and passed through an Affi-Prep Polymixin Matrix column (Bio Rad) to remove endotoxin from the sample. Using the dog portacaval shunt model, the biological activity of the *E. coli* derived ALR was also confirmed.

C. Construction of *S. cerevisiae*

Expression Vector pYEU(A-ALR26)

To express the cloned cDNA ALR26-5 in *Saccharomyces cerevisiae* cells and obtain the gene product in the culture medium, an expression vector was constructed as follows. The protein coding sequence of the ALR26-5 cDNA was inserted just downstream of the polyhistidine sequence and a specific five amino acid cleavage site by enterokinase (DDDDK SEQ ID NO:21) (expression vector pRSET-A, Invitrogen) for the single-step purification by immobilized metal affinity chromatography using the PCR-based in vitro mutagenesis technique as described above in Section A for the COS mammalian expression vector. Upstream of this fragment the signal sequence of wheat alpha-amylase was inserted for secretion, and then a generated fragment was inserted downstream of the gal promoter in the expression vector pYEUra3 (Clontech).

Figure 9:
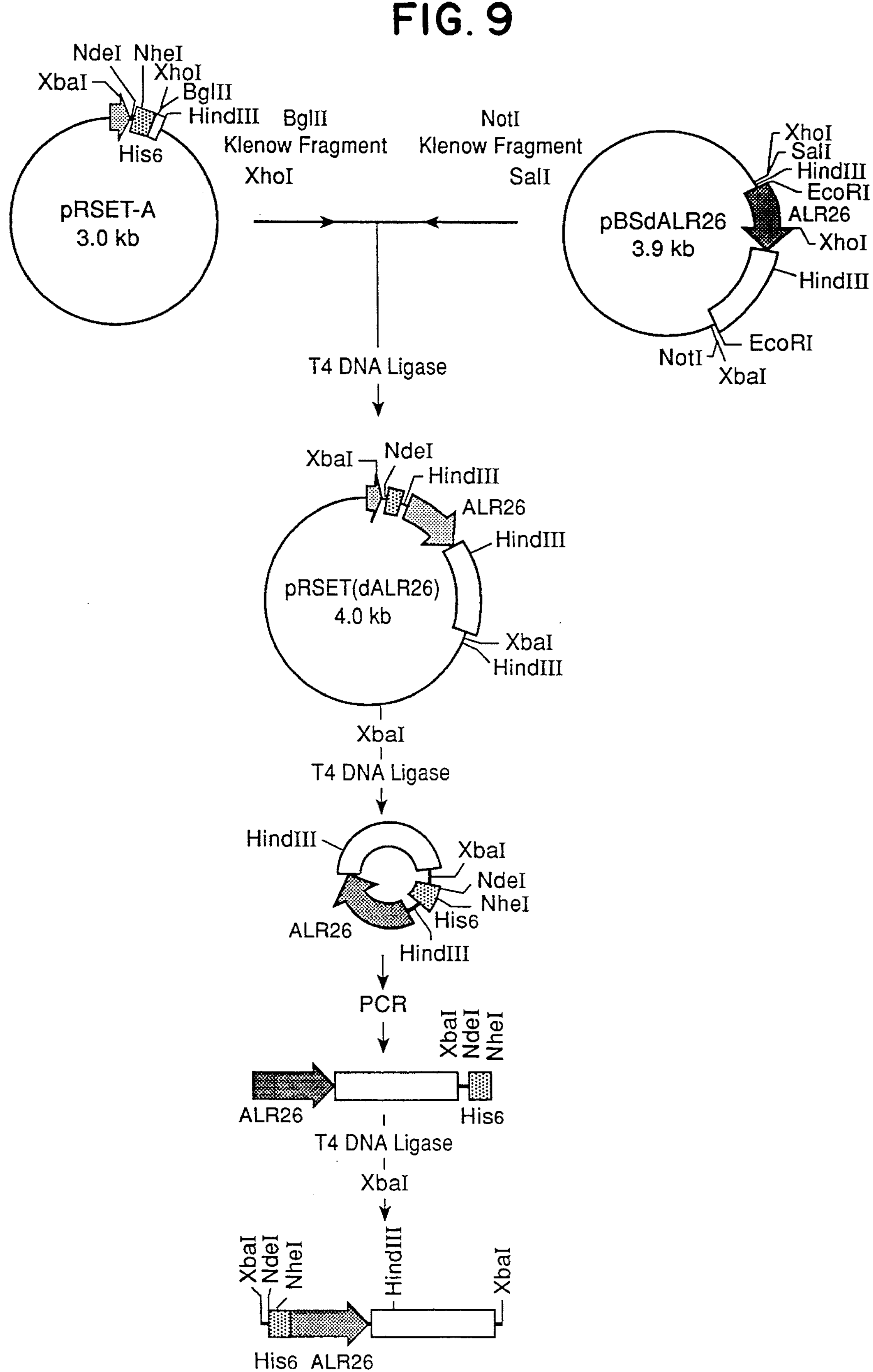
FIG. 9 is a schematic representation of the preparation of plasmid pRSET(dALR26) and the polyhistidine sequence—ALR cDNA sequence used in the preparartion of plasmid pYEU(A-ALR26).
Figure 10:
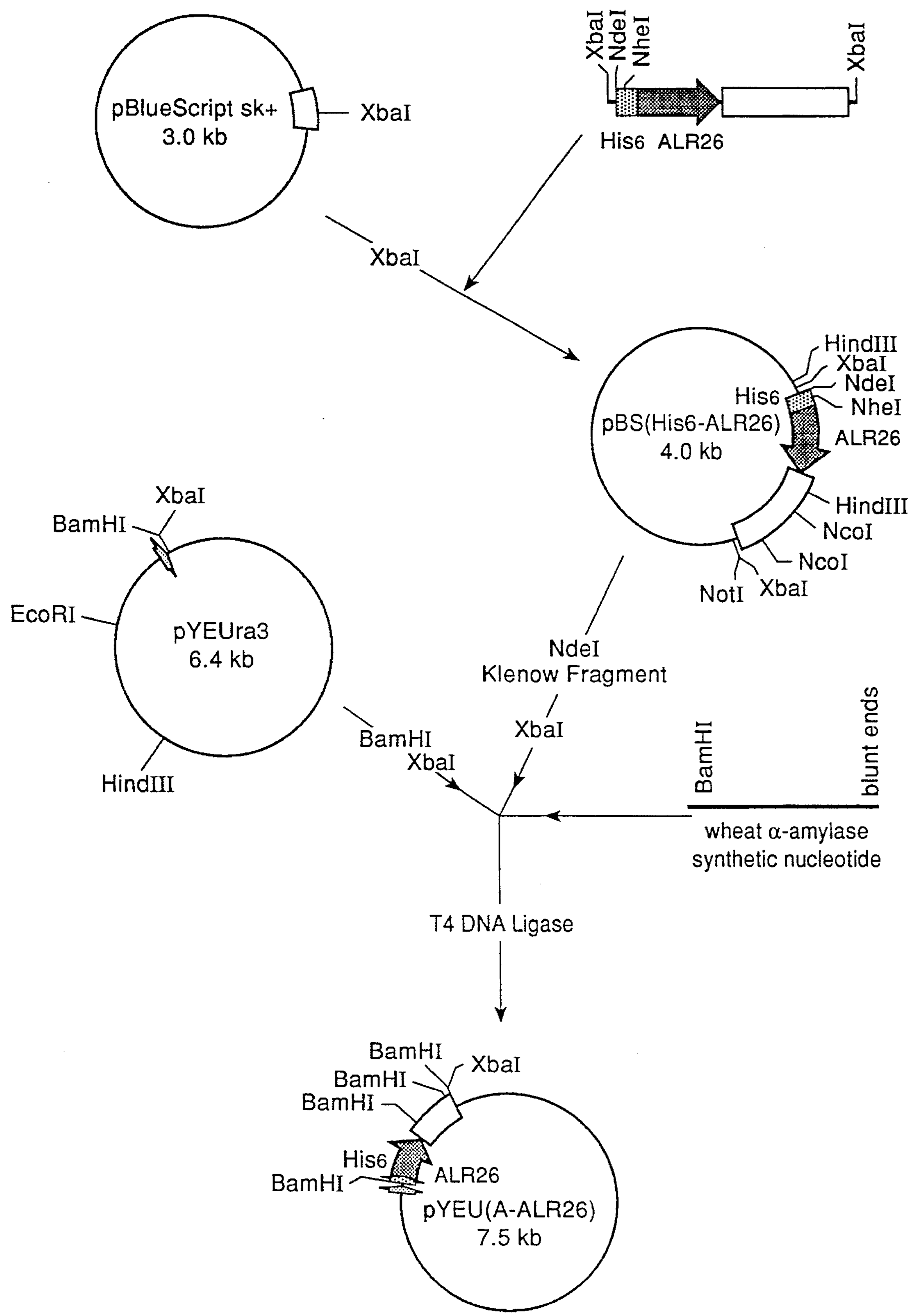
FIG. 10 is a schematic representation of the preparation of plasmid pYEU(A-ALR26) used to express ALR cDNA in *S. cerevisiae.*

The SalI and blunt/ended NotI fragment of ALR26-5 cDNA was inserted into XhoI and blunt/ended BglII site which is located downstream of the polyhistidine and enterokinase cleavage site (FIG. 9). Then, plasmid pRSET-(dALR26) was digested with XbaI, and self-ligated to generate the template for the PCR procedure. The PCR procedure was performed with Pfu DNA polymerase (Stratagene) and synthetic primers 5'-ATGCGGACC CAGCAGAAG-3' (SEQ ID NO:16) and 5'-CTTATCGTCATC GTCGTACA-3' (SEQ ID NO:18) which were based on the nucleotide sequence around the translational initiation site of the ALR26 and the enterokinase cleavage site of pRSET-A, respectively. The PCR product was self-ligated and digested with XbaI, then ligated to the XbaI site of the pBluescript SK+; and the plasmid pBS (His6-ALR26) was obtained. The complementary synthetic nucleotides of wheat alpha-amylase signal sequence, 5'-GATCATG GCGAACAAACACT-TGTCCCTCTCCCTCTTCCTCGTCCTCCT-TGGCCTGTC GGCCAGCTTGGCCTCCGG-3' (SEQ ID NO:19) and 5'-CCGGAG GCCAAGCTGGCCGACAGGC-CAAGGAGGACGAGGAAGAGGGAGAGGGACAA GTGTTTGTTCGCCAT-3' (SEQ ID NO:20) were synthesized. The signal sequence generated by annealing of the above two fragments was ligated in BamHI and XbaI sites of the pYEUra3 together with the XbaI and blunt/ended NdeI fragment of plasmid pBS(His6-ALR26). The resulting plasmid pYEU(A-ALR26), FIG. 10, was used to express the ALR cDNA in *S. cerevisiae.*

*S. cerevisiae* DBY747 cells (Yeast Genetic Stock Center, Berkeley, Calif.) were transformed according to the method of Hinnen (39) with expression vector pYEU (A-ALR26) obtained above. The transformant was inoculated in five ml YEPD medium (5% yeast extract, 2% peptone and 2% glucose) and incubated overnight. 500 μl of the culture was inoculated in 50 ml YEPD medium for eight hours. The culture medium was collected by centrifugation, adjusted to 500 mM NaCl and pH 8.0 with $KPO_4$, loaded onto a two ml ProBond metal affinity column (Invitrogen) pre-equilibrated with a buffer (40 mM $KPO_4$, pH 8.0, 500 mM NaCl) and washed four times in the same buffer. ALR was eluted with four ml of elution buffer (40 mM $KPO_4$, pH 4.0, 500 mM NaCl) and was concentrated by centrifugation on a 10,000 MW cutoff Centricon-10 (Amicon). The protein was treated with two μg of enterokinase in a buffer (10 mM Tris pH 8.0, 10 mM $KPO_4$). Using the dog portacaval shunt model, the biological activity of *S. cerevisiae* derived ALR was confirmed.

D. In Vivo Testing of Recombinant ALR

As mentioned above, after the ALR expression vector was transfected into COS-1 cells, the cells were cultured and proteins harvested from both the culture supernatant and the cytosolic fraction from the COS cell homogenate. Both samples were tested for ALR activity in the Eck's fistula model (Table 4). A dose-dependent stimulation of DNA synthesis was detected in the cytosolic fraction but not in the culture supernatant. This activity was abolished by the anti-ALR monoclonal antibody (Table 4).

Similar results were obtained when the *E. coli* or the *S. cerevisiae* derived recombinant ALR was assayed in the dog portacaval shunt model.

POTENTIAL SCIENTIFIC AND THERAPEUTIC APPLICATIONS OF ALR

The number of growth factors with demonstrable in vivo hepatotrophic activity (see Table 2) is small. Unlike all of the other putative hepatotrophic substances, the augmenter of regeneration (ALR) is the product of regeneration, not something that has been used to cause it. An intriguing question has been what is the nature of ALR. Now that the ALR gene and recombinant molecule are available (this patent application), this question is susceptible to analysis, as well as the physiologic significance of the protein. We expect an immediate linkage with experimental oncology, research on aging, and the interphase between immunology and growth control.

The most obvious immediate clinical implication for any new liver specific growth factor is its use for the treatment of hepatic failure—to promote the regeneration upon which clinical recovery depends (40,41). With currently available growth factors, this has been an unfulfilled fantasy, not only because there are so few of these substances, but because they can only initiate, not govern and perpetuate regeneration. Whether ALR can go beyond this therapeutically will have to be determined by direct experimentation and then clinical trial.

The governance of regeneration once begun, including its perpetuation and control, has not been understood but has been postulated to be by two broad mechanisms. One is directly biochemical involving interlocking phosphorylation-dephosphorylation pathways with protein kinase (tyrosine, serine, threonine) way stations connecting cell surface receptors to the nucleus and ultimately gene expression products from the nucleus. The other is immunologic whereby these gene products control the major histocompatibility complex (MHC) gene products and alter MHC Class II expression of non-parenchymal cells of the liver which ultimately control hepatocyte proliferation through an interactive cytokine/growth factor network. With recombinant ALR and development of molecular probes, such receptor-reactor networks can now be systematically examined.

Similarly, pathologic growth (cancer) will be susceptible to analysis in the field of oncology. Of great interest will be the determination of anti-ALR effects of specific monoclonal antibodies which now can be raised with the recombinant ALR. Also, the availability of the gene will permit the prompt creation of transgenic animals, and study of the physiologic effect of the new gene in these animals.

Finally, we have emphasized throughout this patent application the interspecies nature of ALR, exemplified by the retention of full potency of rat ALR in the phylogenetically distant dog which allowed us to develop an interspecies assay system (The Eck's fistula model). We are therefore certain that human ALR is highly or greater homologous with rat ALR and consider this patent application to include the impending next step of production of the human ALR gene and its protein expression product.

Human-derived ALR cDNA can be extracted from isolated clones by screening cDNA libraries prepared from mRNA of human liver with rat derived ALR cDNA or genomic DNA as the probe. Also, human-derived ALR cDNA can be prepared from isolated clones by screening the cDNA libraries constructed from mRNA extracted from human liver. The screening of the cDNA library can be carried out by using as the synthetic oligonucleotides, the human ALR cDNA or the human ALR genomic DNA obtained in accordance with the present invention or by using antibodies against human ALR. The oligonucleotides used as probes can be synthesized on the basis of the deduced nucleotide sequence from the human ALR amino acid sequence as has been done in the present invention for the rat ALR.

The extension of this patent application to the human gene will have a conventional purpose. Although the rat ALR can be used for clinical purposes (most sera or anti-lymphocyte glogulins and even commercial insulin are heterologous proteins), slight interspecies differences in the amino acid sequence of a protein can cause immune reactions, often limiting the duration of treatment with a given protein. The human ALR when it is available would avoid this kind of complication.

REFERENCES

The following publications were cited above and are incorporated herein by reference:

1. Starzl TE, Kaupp HA Jr, Brock DR, Lazarus RE, Johnson RV: Reconstructive problems in canine liver homotransplantation with special reference to the postoperative role of hepatic venous flow. Surg Gynecol Obstet 111:733–743, 1960.
2. Starzl TE, Marchioro TL, Rowlands DT Jr, Kirkpatrick CH, Wilson WEC, Rifkind D, Waddell WR: Immunosuppression after experimental and clinical homotransplantation of the liver. Ann Surg 160:411–439, 1964.
3. Marchioro TL, Porter KA, Dickinson TC, Faris TD, Starzl TE: Physiologic requirements for auxiliary liver homotransplantation. Surg Gynecol Obstet 121:17–31, 1965.
4. Marchioro TL, Porter KA, Brown BI, Otte J-B, Starzl TE: The effect of partial portacaval transposition on the canine liver~Surgery 61:723–732, 1967.
5. Starzl TE, Francavilla A, Halgrimson CG, Francavilla FR, Porter KA, Brown TH, Putnam CW: The origin, hormonal nature, and action of hepatotrophic substances in portal venous blood. Surg Gynecol Obstet 137:179–199, 1973.
6. Starzl TE, Porter KA, Kashiwagi N, Lee IY, Russell WJI, Putnam CW: The effect of diabetes mellitus on portal blood hepatotrophic factors in dogs. Surg Gynecol Obstet 140:549–562, 1975.
7. Starzl TE, Porter KA, Francavilla A: The Eck fistula in animals and humans. Curr Probl Surg 20:687–752, 1983.
8. Starzl TE, Porter KA, Putnam CW: Intraportal insulin protects from the liver injury of portacaval shunt in dogs. Lancet 2:1241–1246, 1975.
9. Starzl TE, Watanabe K, Porter KA, Putnam CW: Effects of insulin, glucagon, and insulin/glucagon infusions on liver morphology and cell division after complete portacaval shunt in dogs. Lancet 1 (No.7964):821–825, 1976.
10. Leffert HL: Growth control of differentiated fetal rat hepatocytes in primary monolayer culture—VII, hormonal control of DNA synthesis and its possible significance to the problem of liver regeneration. J Cell Biol 62:792, 1974.
11. Leffert H, Alexander NM, Faloona G, Rubalcava B, Unger R: Specific endocrine and hormonal receptor changes associated with liver regeneration in adult rats. Proc Natl Acad Sci USA 72:4033–4036, 1975.
12. Honey RW: Control of growth of mammalian cells in cell culture. Nature 258:487–490, 1975.
13. Bucher NLR, Swaffield MN: Regulation of hepatic regeneration in rats by synergistic action of insulin and glucagon. Proc Natl Acad Sci USA 72:1157–1160, 1975.
14. Whittemore AD, Kasuya M, Voorhees AB Jr, Price JB Jr: Hepatic regeneration in the absence of portal viscera. Surgery 77:419, 1975.
15. Duguay LR, Orloff MJ: Regulation of liver regeneration by the pancreas in dogs. Surg Forum 27:355–357, 1976.
16. MacManus JP, FranKs W, Youdale T, Braceland BM: Increases in rat liver cyclic AMP concentrations prior to the initiation of DNA synthesis following partial hepatectomy or hormone infusion. Biochem Biophys Res Commun 49(5):1201–1207, 1972.
17. Thrower S, Ord MG: Hormonal control of liver regeneration. Biochem J 144:361–369, 1974.
18. Byus CV, Hedge GA, Russell DH: The involvement of cyclic AMP dependent protein kinase(s) in the induction of ornithine decarboxylase in the regenerating rat liver and in the adrenal gland after unilateral adrenalectomy. Biochim Biophys Acta 498(1):39–45, 1977.
19. Francavilla A, Starzl TE, Porter K, Scotti-Foglieni C, Michalopoulos GK, Carrieri G, Trejo J, Azzarone A, Barone M, Zeng Q: Screening for candidate hepatic growth factors by selective portal infusion after canine eck fistula. Hepatology 14:665–670, 1991.
20. Michalopoulos G, Cianciulli HD, Novotny AR, et al: Liver regeneration studies with rat hepatocytes in primary culture. Cancer Res 42:4673–4682, 1982.
21. Nakamura T, Nawa K, Ichihara A: Partial purification and characterization of hepatocyte growth factor from serum of hepatectomized rats. Biochem Biophys Res Commun 122:1450–1459, 1984.
22. Starzl TE, Jones AF, Terblanche J, Usui S, Porter KA, Mazzoni G: Growth-stimulating factor in regenerating canine liver. Lancet 1:127–130, 1979.
23. Teir H, Ravanti K: Mitotic activity and growth factors in the liver of the whole rat. Exp Cell Res 5:500–507, 1953.
24. Blomqvist K: Growth stimulation in the liver and tumor development following intraperitoneal injections of liver homogenates in the rat. Act a Pathol Microbiol Scand 121 (Suppl) 121, 1957.
25. LaBrecque DR, Pesch LA: Preparation and partial characterization of hepatic regenerative stimulator substance (SS) from rat liver. J Physiol 248:273–284, 1975.
26. Terblanche J, Porter KA, Starzl TE, Moore J, Patzelt L, Hayashida N: Stimulation of hepatic regeneration after partial hepatectomy by infusion of a cytosol extract from regeneration dog liver. Surg Gynecol Obstet 151:538–544, 1980.

27. Francavilla A, Porter KA, Benichou J, Jones AF, Starzl TE: Liver regeneration in dogs: Morphologic and chemical changes. J Surg Res 25:409–419, 1978.

28. Francavilla A, Barone M, Van Thiel DH, Mazzaferro V, Prelich J, Starzl TE: Further steps of HSS (hepatic stimulatory substance) purification. Dig Dis Sci 36 (5):674–680, 1991.

29. Francavilla A, Ove P, Polimeno L, Coetzee M, Makowka L, Rose J, Van Thiel DH, Starzl TE: Extraction and partial purification of hepatic stimulatory substance in rats, mice and dogs. Cancer Res 47:5600–5605, 1987.

30. Starzl TE, Lee IY, Porter KA, Putnam CW: The influence of portal blood upon lipid metabolism in normal and diabetic dogs and baboons. Surg Gynecol Obstet 140:381–396, 1975.

31. Chomczynski P, Sacchi N: Single step method of RNA isolation by acid guanidinium thiocyanate-phenol-chloroform extraction. Anal Biochem 162 (1):156–159, 1987.

32. Sanger F, Nicklen S, Coulson AR: DNA sequencing with chain terminating inhibitors. Proc Natl Acad Sci USA 74 (12): 5463–5467, 1977.

33. Marchuk D, Drumm M, Saulino A, Collins FS: Construction of Tvectors, a rapid and general system for direct cloning of unmodified PCR products. Nucl Acids Res 19 (5):1154, 1991.

34. Maniatis T, Fritsch EF, Sambroak J: Molecular cloning; A laboratory manual (Cold Spring Harbor Lab, Cold Spring Harbor, N.Y.), 1982.

35. Lisowsky T: Dual function of a new nuclear gene for oxidative phosphorylation and vegetative growth in yeast. Mol Gen Genet 232:58–64, 1992.

36. Matsumoto K, Takehara T, Inoue H, Hagiya M, Shimizu S, Nakamura T: Deletion of kringle doming or the N-terminal hairpin structure in hepatocyte growth factor results in marked decreases in related biological activities. Biochem Biophys Res Comm 181 (2):691–699, 199 1 .

37. Seed B: An LFA-3 cDNA encodes a phospholipid-linked membrane protein homoloqous to its receptor CD2. Nature 329 (6142):840–842, 1987.

38. Yokota T, Lee F, Rennick D, Hall C, Arai N, Mossmann T, Nabel G, Canter H, Arai K: Isolation and characterization of a mouse cDNA clone that express mast-cell growth-factor activity in monkey cell. Proc Natl Acad Sci USA 81:1070–1074, 1984.

39. Hinnen A, Hicks JB, Fink GR: Transformation of yeast. Proc Natl Acad Sci USA 75 (4):1929–1933, 1978.

40. Lee WM: Acute liver failure. New Eng J Med 329:1862–1872, 1993.

41. Francavilla A, DiLeo A, Polimeno L, Gavaler J, Pellicci R, Todo S, Kam I, Prelich J, Makowka L, Starzl TE: The effect of hepatic stimulatory substance, isolated from regenerating hepatic cytosol, and 50,000 and 300,000 subfractions in enhancing survival in experimental acute hepatic failure in rats treated with D-Galactosamine. Hepatology 6 (6):1346–1351, 1986.

42. PCR Protocols—A Guide to Methods and Application, Innis et al. editors, Academic Press, New York, 1990.

TABLE 1

HEPATOTROPHIC EFFECTS OF INSULIN (WITH OR WITHOUT GLUCAGON): 4-DAY ECK FISTULA EXPERIMENT

| | Labelled Left | Hepatocytes/ 1000 Right | Cell Size Left | Units Right |
|---|---|---|---|---|
| Normal Liver | 1.5 | 1.5 | .17 | .17 |
| Saline and Eck Fistula | 4.5 | 4.5 | .09 | .09 |
| Insulin (0.43/kg/d) | 16.0 | 5.0 | .17 | .09 |
| Insulin (0.16u/kg/d) | 15.0 | 5.0 | .17 | .09 |
| Glucagon (0.6 mg/kg/d) | 4.5 | 4.5 | .09 | .09 |
| Glucagon (0.005 mg/kg/d) | 4.5 | 4.5 | .09 | .09 |
| 2:1 Insulin/ Glucagon | 16.0 | 4.5 | .17 | .09 |
| 2:100 Insulin/ Glucagon | 15.0 | 4.5 | .11 | .07 |

*Insulin protection maintained for duration of insulin supply (at least 60 days).

TABLE 2

GROWTH FACTORS REHEALED BY ECK FISTULA (1993)

| | REFERENCE |
|---|---|
| STIMULATORY | |
| HORMONES: | |
| INSULIN | 1, 3, 10 |
| GROWTH FACTORS: | |
| CYTOSOL (AND ALR) | 4, 5 |
| IGF II | 19 |
| TGF-ALPHA* | 19 |
| HGF* | 19 |
| IMMUNOSUPPRESSANTS: | |
| CYCLOSPORINE | 19 |
| FK 506 | 19 |
| IMMUNOPHILINS: | |
| FKBP12 | |
| INHIBITORY | |
| GROWTH FACTORS: | |
| TGF CYTOKINE** | 19 |
| IMMUNOSUPPRESSION: | |
| RAPAMYCIN** | 19 |

*MITOGENIC IN TISSUE CULTURE
**INHIBITORY IN TISSUE CULTURE

TABLE 3

Steps of Purification and Biological Activity of ALR from Weanling Rat Liver Tested in Rat with 40% Partial Hepatectomy

| Material Injected | Protein (μg/RAT) | DNA synthesis (CPM/mg DNA) | Purification-fold |
|---|---|---|---|
| Cytosol | $7.5 \times 10^4$ | 43,350 ± 8,820 | |
| OH—F | $1.0 \times 10^4$ | 66,350 ± 11,350 | 15 |
| 30 kDa-F | $0.27 \times 10^4$ | 63,520 ± 13,220 | 52 |
| $F_{150}$ | 3 | 54,380 ± 10,200 | 38,100 |
| P-$F_{150}$ | 1 | 53,280 ± 7,900 | 110,000 |
| Acr-$F_4$ | $3 \times 10^{-1}$ | 49,350 ± 7,084 | 330,000 |

TABLE 4

EFFECT ON LIVER REGENERATION OF RECOMBINANT ALR INFUSED INTO LEFT LOBE OF PORTACAVAL DOGS WITH AND WITHOUT MONOCLONAL ANTIBODY

| Sample | Number of labelled hepatocytes per 1000 hepatocytes | |
|---|---|---|
| | L Lobe | R Lobe |
| Vector supernatant to left | 3.8 | 4.0 |
| Vector cytosol to left | 6.3 | 5.4 |
| ALR supernatant: 40 ng/kg to left | 6.4 | 6.6 |
| ALR cytosol: 20 ng/kg to left | | |
| ALR cytosol: 20 ng/kg + anti-ALR mAB to right | 10.1 | 5.1 |
| ALR cytosol: 40 ng/kg to left | 15.2 | 4.8 |

What is claimed is:

1. An isolated DNA comprising a nucleotide sequence encoding mammalian augmenter of liver regeneration, wherein said DNA has the nucleotide sequence of SEQ ID NO:1.

2. An isolated DNA comprising a nucleotide sequence encoding mammalian augmenter of liver regeneration., wherein said DNA has the nucleotide sequence of SEQ ID NO:3.

3. A recombinant expression vector containing an exogenous DNA sequence encoding mammalian augmenter of liver regeneration wherein the vector is capable of expressing augmenter of liver regeneration in a transformed microorganism or host cell and wherein said augmenter of liver regeneration has the amino acid sequence described in SEQ ID NO:2.

4. A microorganism transformed with the vector of claim 3, wherein said microorganism is capable of expressing augmenter of liver regeneration.

5. The transformed microorganism of claim 4, wherein said microorganism is *E. coli.*

6. The transformed microorganism of claim 4, wherein said microorganism is yeast.

7. A host cell capable of expressing augmenter of liver regeneration obtained by transforming a mammalian cell line with said vector of claim 3.

8. The host cell of claim 7, wherein said cell is selected from the group consisting of COS-1, CHO and C127.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 1225 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
CGCGCGCTGG CGGTGGCATG CGCGCTGCTC TGTCCCGTCT CCTGCACGCC CTCTTGGCCC   60
CGCTGCTCGT ACGCCAGCAA TATGGCGGCG CCCAGCGAAC CCGCAGGTTT CCCTCGCGGC  120
AGTCGCTTCT CCTTCCTGCC GGGCGGCGCG CACTCGGAGA TGACCGACGA CCTGGTGACT  180
GACGCGCGGG GCCGCGGCGC AAGGCATAGA AAAGACAACG CCCCTGCCGC GGCCCCGGCG  240
CCGAAAGGTT TGGAGCACGG GAAGCACCGT GCCGGGCCTG CGTGGACTTC AAGTCGTGGA  300
TGCGGACCCA GCAGAAGCGG GACATCAAGT TTAGGGAGGA CTGTCCACAG GATCGGGAAG  360
AATTGGGTCG CAACACCTGG GCTTTCCTTC ATACGCTGGC CGCCTATTAC CCGGACATGC  420
CCACGCCAGA ACAACAGCAG GATATGGCCC AGTTCATACA TATATTTTCC AAGTTTTACC  480
CCTGTGAGGA GTGTGCAGAA GACATAAGGA AGAGGATAGA CAGGAGCCAG CCAGACACAA  540
GCACTCGAGT GTCCTTCAGC CAGTGGCTGT GCCGCCTTCA CAATGAAGTG AACCGGAAGC  600
TGGGCAAGCC TGATTTTGAC TGCTCAAGAG TTGATGAGCG ATGGCGTGAC GGCTGGAAGG  660
ACGGCTCCTG TGACTAAGGA TTACCACAGA CCGTGCAGGG CAACGCCGGG TTCTATGGGC  720
AACAGCCTGA CTGACGATTA AAGTGCATCT GAGCCAAAGC TTGTTTCTGT GGTGGGGGTG  780
GGATCCCCTA GAACACTGCC TATGGGAACC CTACCCACAG ACTCAGAAAC GGAGGTGCCC  840
ACTATAGACA GTTGGGTGGC TTCCTCAGGT CTTAAAGCCC CATGGGACTG AAGATGAGAG  900
GCAGGAGTGG TCCAGGGCAC CCCATACCCC TTATGATACC CATTATACAT TTGGGACATA  960
GTTGCCTCAA AGGAAGGTGG GCTAGACCAT TGCCTTCCTA CTACATATCC CCAGCTGCCT 1020
ACAGAACTGT GACCCAGGCA ACTCTGCCAT TTCAGAATTG AAGCAGGGTT CCAGCTCTAG 1080
TTGGGTTTTT CTCTTAGGGT AAACCAACCA TGGTGCCCAC TGTCAGCCTG GCACATGGTC 1140
TTCTGCAGCC AGGACAAACA TGTCAGCAGA GGATCCTGGG AAGGGCTTCC TTAGCGTTTG 1200
```

-continued

AGACCAAAAT AAAATGAAGT GACTT 1225

( 2 ) INFORMATION FOR SEQ ID NO:2:

( i ) SEQUENCE CHARACTERISTICS:
( A ) LENGTH: 125 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Met Arg Thr Gln Gln Lys Arg Asp Ile Lys Phe Arg Glu Asp Cys Pro
1               5                   10                  15

Gln Asp Arg Glu Glu Leu Gly Arg Asn Thr Trp Ala Phe Leu His Thr
            20                  25                  30

Leu Ala Ala Tyr Tyr Pro Asp Met Pro Thr Pro Glu Gln Gln Gln Asp
        35                  40                  45

Met Ala Gln Phe Ile His Ile Phe Ser Lys Phe Tyr Pro Cys Glu Glu
    50                  55                  60

Cys Ala Glu Asp Ile Arg Lys Arg Ile Asp Arg Ser Gln Pro Asp Thr
65                  70                  75                  80

Ser Thr Arg Val Ser Phe Ser Gln Trp Leu Cys Arg Leu His Asn Glu
                85                  90                  95

Val Asn Arg Lys Leu Gly Lys Pro Asp Phe Asp Cys Ser Arg Val Asp
            100                 105                 110

Glu Arg Trp Arg Asp Gly Trp Lys Asp Gly Ser Cys Asp
        115                 120                 125
```

( 2 ) INFORMATION FOR SEQ ID NO:3:

( i ) SEQUENCE CHARACTERISTICS:
( A ) LENGTH: 375 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:3:

```
ATGCGGACCC AGCAGAAGCG GGACATCAAG TTTAGGGAGG ACTGTCCACA GGATCGGGAA   60
GAATTGGGTC GCAACACCTG GGCTTTCCTT CATACGCTGG CCGCCTATTA CCCGGACATG  120
CCCACGCCAG AACAACAGCA GGATATGGCC CAGTTCATAC ATATATTTTC CAAGTTTTAC  180
CCCTGTGAGG AGTGTGCAGA AGACATAAGG AAGAGGATAG ACAGGAGCCA GCCAGACACA  240
AGCACTCGAG TGTCCTTCAG CCAGTGGCTG TGCCGCCTTC ACAATGAAGT GAACCGGAAG  300
CTGGGCAAGC CTGATTTTGA CTGCTCAAGA GTTGATGAGC GATGGCGTGA CGGCTGGAAG  360
GACGGCTCCT GTGAC                                                   375
```

( 2 ) INFORMATION FOR SEQ ID NO:4:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

-continued

Phe Tyr Pro Xaa Glu Glu Xaa Ala Glu Asp Ile
1 5 10

( 2 ) INFORMATION FOR SEQ ID NO:5:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Leu Gly Lys Pro Asp Phe Asp Xaa Ser Xaa Val
1 5 10

( 2 ) INFORMATION FOR SEQ ID NO:6:

( i ) SEQUENCE CHARACTERISTICS:
( A ) LENGTH: 22 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Xaa Ile Asp Arg Ser Gln Pro Asp Thr Ser Thr Arg Val Ser Phe Xaa
1 5 10 15

Gln Xaa Leu Xaa Xaa Leu
20

( 2 ) INFORMATION FOR SEQ ID NO:7:

( i ) SEQUENCE CHARACTERISTICS:
( A ) LENGTH: 45 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

AACTGGAAGA ATTCGCGGCC GCAGGAATTT TTTTTTTTT TTTTT 45

( 2 ) INFORMATION FOR SEQ ID NO:8:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

ATNGAYCGNA GYCARCCNGA YAC 23

( 2 ) INFORMATION FOR SEQ ID NO:9:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:9:

ATNGAYCGNT CNCARCCNGA YAC 23

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

ATNGAYAGRA GYCARCCNGA YAC 23

( 2 ) INFORMATION FOR SEQ ID NO:11:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

ATNGAYAGRT CNCARCCNGA YAC 23

( 2 ) INFORMATION FOR SEQ ID NO:12:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Ile Asp Arg Ser Gln Pro Asp Thr
1 5

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

GCCGCAGGAA TTTTTTTTTT 20

( 2 ) INFORMATION FOR SEQ ID NO:14:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

-continued

TGGACTTCAA GTCGTGGATG 20

( 2 ) INFORMATION FOR SEQ ID NO:15:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

GAATTCGATA TCAAGCTTAT CG 22

( 2 ) INFORMATION FOR SEQ ID NO:16:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

ATGCGGACCC AGCAGAAG 18

( 2 ) INFORMATION FOR SEQ ID NO:17:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

ATTCTGTTTT CCTGTGTGAA ATT 23

( 2 ) INFORMATION FOR SEQ ID NO:18:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

CTTATCGTCA TCGTCGTACA 20

( 2 ) INFORMATION FOR SEQ ID NO:19:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

GATCATGGCG AACAAACACT TGTCCCTCTC CCTCTTCCTC GTCCTCCTTG GCCTGTCGGC 60

CAGCTTGGCC TCCGG 75

-continued ( 2 ) INFORMATION FOR SEQ ID NO:20:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

CCGGAGGCCA AGCTGGCCGA CAGGCCAAGG AGGACGAGGA AGAGGGAGAG GGACAAGTGT 60

TTGTTCGCCA T 71

( 2 ) INFORMATION FOR SEQ ID NO:21:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:21:

Asp Asp Asp Asp Lys
1 5